(12) United States Patent
Bomber et al.

(10) Patent No.: US 6,370,972 B1
(45) Date of Patent: Apr. 16, 2002

(54) CHEMICAL SAMPLING SINK

(75) Inventors: Andrew J. Bomber; Michael A. Hamilton, both of Vancouver, WA (US)

(73) Assignee: SEH America, Inc., Vancouver, WA (US)

( * ) Notice: Subject to any disclaimer, the term of this patent is extended or adjusted under 35 U.S.C. 154(b) by 0 days.

(21) Appl. No.: 09/386,499

(22) Filed: Aug. 30, 1999

(51) Int. Cl.$^7$ ................................................ G01N 1/00
(52) U.S. Cl. .................................................. 73/863.23
(58) Field of Search ..................... 73/863.23, 864.34; 436/177; 454/56, 57; 141/93; 422/199

(56) References Cited

U.S. PATENT DOCUMENTS

| | | | | |
|---|---|---|---|---|
| 3,072,040 A | * | 1/1963 | Triplett ........................ | 454/56 |
| 4,345,615 A | * | 8/1982 | Di Cicco et al. ............ | 137/343 |
| 5,295,902 A | * | 3/1994 | Hock ............................ | 454/57 |
| 5,395,429 A | * | 3/1995 | Sutsko et al. ................ | 95/273 |
| 5,441,708 A | * | 8/1995 | Diccianni et al. ............ | 422/292 |
| 5,730,765 A | * | 3/1998 | Henry et al. .................. | 55/270 |
| 5,924,921 A | * | 7/1999 | Yang ............................ | 454/253 |

OTHER PUBLICATIONS

Valves, Manual, *Instrumentation PFA Products*, Bulletin 4181 USA Revised, Oct. 1996, p. 2.

* cited by examiner

*Primary Examiner*—Hezron Williams
*Assistant Examiner*—Dennis Loo
(74) *Attorney, Agent, or Firm*—Alston & Bird LLP (57) ABSTRACT

A chemical sampling sink and method. The chemical sampling sink typically includes an enclosure configured to contain a receptacle, and a chemical supply line extending into the enclosure, the chemical supply line including a dispenser configured to deliver a liquid chemical to the receptacle. The chemical sampling sink also includes an exhaust line attached to the enclosure, the exhaust line being configured to suction gases from the enclosure, and a filter positioned on the enclosure, the filter being configured to remove contaminants from air drawn into the enclosure as gases are suctioned from the enclosure out the exhaust line.

38 Claims, 8 Drawing Sheets

CHEMICAL SAMPLING SINK

TECHNICAL FIELD

The present invention relates generally to chemical sampling sinks, and more specifically to chemical sampling sinks for use in the silicon processing industry.

BACKGROUND

Chemical sampling sinks are used in a variety of industrial applications to take samples of chemicals in a controlled environment, free of pollutants. In the semiconductor processing industry, chemical sampling sinks are used to take samples of high purity chemicals, such as ammonium hydroxide, as a quality control measure. The samples are analyzed to ensure that the purity of the chemical is within a desired range.

To prevent contaminants from entering the sample, current chemical sampling sinks include an enclosure surrounding a liquid chemical dispenser. The enclosure includes a door through which a receptacle may pass to be positioned below the dispenser. Once the receptacle is inserted, the door may be shut and chemical poured from the dispenser.

Current chemical sampling sinks include a drain to carry away spilled or overflowing liquids, and an exhaust to draw air out of the enclosure. One problem with current chemical sampling sinks is that the exhaust systems tend to draw contaminated air into the enclosure. In silicon processing environments, fine silicon dust, present in minute amounts in the air, may find its way into the enclosure through gaps in the enclosure walls or door, thereby contaminating the sample. Other contaminants, such as dirt and pollen, may also be drawn into the enclosure through the gaps. Because chemical sampling sinks are used to take samples of extremely high purity chemicals, even minute amounts of contaminants can ruin a sample.

Another problem with current chemical sampling sinks is that operators of the sinks are able to dispense chemical liquids into receptacles while the door of the enclosure is open. This may expose the sample to airborne contamination entering through the door into the enclosure. In addition, dangerous chemical droplets or gases may be released from the sampling sink through the open door into the environment and/or onto the operator. Because many of the chemicals sampled with chemical sampling sinks are potentially harmful, uncontrolled release of these chemicals is a potential environmental and health risk.

In addition, current chemical sampling sinks are translucent and allow ultraviolet (UV) radiation to enter the interior of the sink and damage components, or the sinks are made of material that deteriorates when exposed to UV radiation. Finally, current chemical sampling sinks use push-button valves, and require operators to continuously press the buttons for lengthy periods of time in order to dispense a sample.

It would be desirable to provide a chemical sampling sink that does not draw airborne contaminants into the enclosure, prevents dispensing of chemicals with the door open, is UV-resistant, and/or does not require an operator to press a button continuously for lengthy periods to dispense a chemical.

SUMMARY

A chemical sampling sink and method are provided. The chemical sampling sink typically includes an enclosure configured to contain a receptacle, and a chemical supply line extending into the enclosure, the chemical supply line including a dispenser configured to deliver a liquid chemical to the receptacle. The chemical sampling sink also includes an exhaust line attached to the enclosure, the exhaust line being configured to suction gases from the enclosure, and a filter positioned on the enclosure, the filter being configured to remove contaminants from air drawn into the enclosure as gases are suctioned from the enclosure out the exhaust line. The sink may also have valves that do not require operators to continuously press a button to dispense chemicals, and the sinks may be made of a material that is UV resistant. Sinks that have new valves or that are UV resistant may or may not include a filter to remove contaminants from air drawn into the enclosure and sinks that include such a filter may or may not have new valves or UV resistant material.

The method typically includes providing an enclosure, placing a receptacle within the enclosure, the receptacle being configured to hold a chemical, dispensing a chemical through a dispenser into the receptacle within the enclosure, suctioning gases from the enclosure to an exhaust line, and filtering air drawn into the enclosure during suctioning.

DETAILED DESCRIPTION

Figure 1:
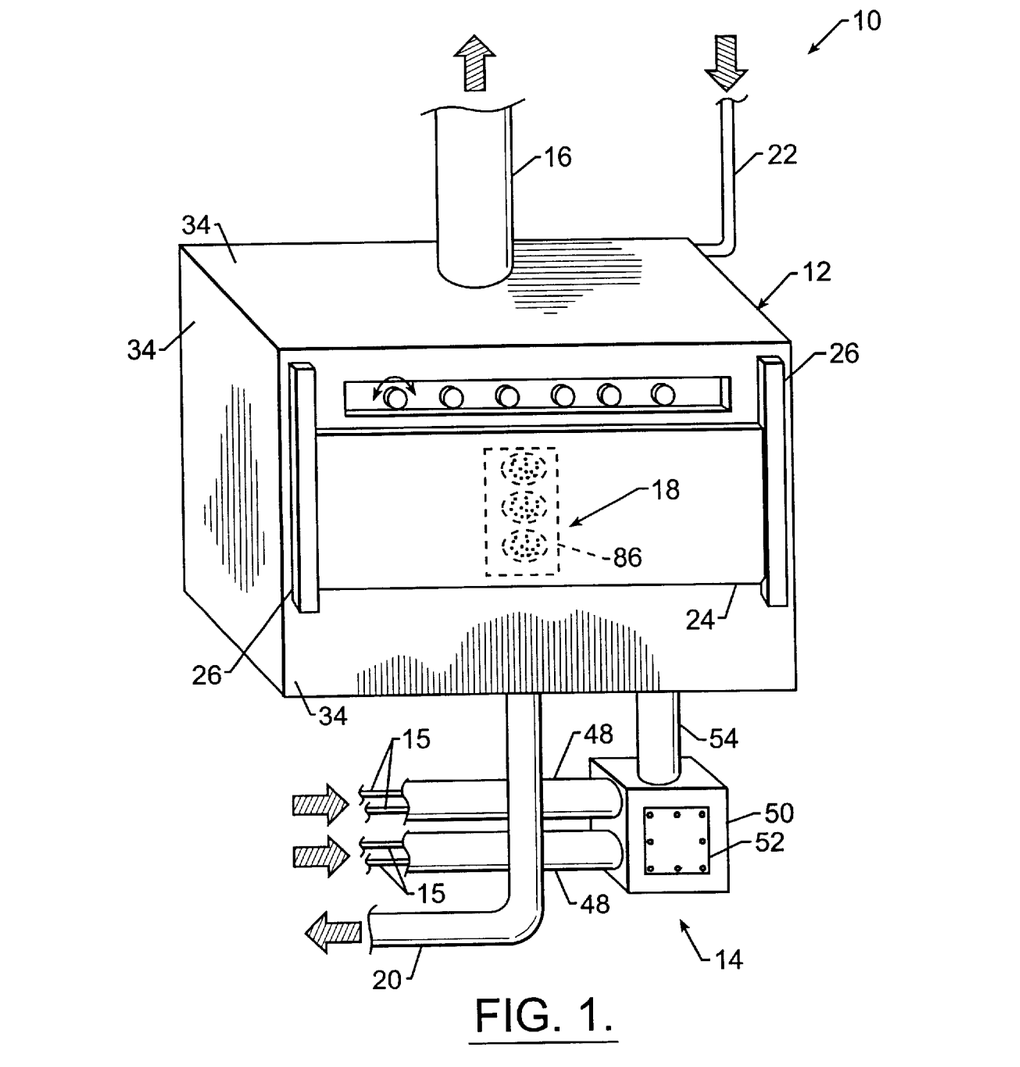
FIG. 1 is an isometric view of one embodiment of a chemical sampling sink according to the present invention.

Referring to FIG. 1, one embodiment of a chemical sampling sink according to the present invention is shown generally at 10. Chemical sampling sink 10 generally includes an enclosure 12, a chemical delivery subsystem 14 including a plurality of chemical supply lines 15 extending into the enclosure, an exhaust line 16 configured to draw exhaust gases from the enclosure, and a filter assembly 18 positioned in a wall of the enclosure. The filter assembly is configured to remove contaminants from air drawn into the enclosure as gases are suctioned from the enclosure through exhaust line 16. Chemical sampling sink 10 also may include a drain 20 and water supply line 22. To take a sample of a chemical, a receptacle 28, shown in FIG. 2, may be placed within enclosure 12 through an access door 24, and a sample quantity of liquid chemical may be dispensed into the receptacle from a dispenser 30.

Enclosure 12 typically includes an outer wall 34 formed in the shape of a box with rectangular sides. Alternatively, outer wall 34 may be formed in the shape of a cube, sphere, or virtually any other shape. Enclosure 12 typically is formed from polypropylene. Alternatively, enclosure 12 may be formed at least partially of metal, glass, and/or other materials, or may be formed of another type of plastic. Where chemical sampling sink 10 is to be exposed to ultraviolet (UV) radiation, such as in outdoor applications, a dark or black plastic, such as black polypropylene may be used to reduce UV damage to the surface and interior components.

Figure 2:
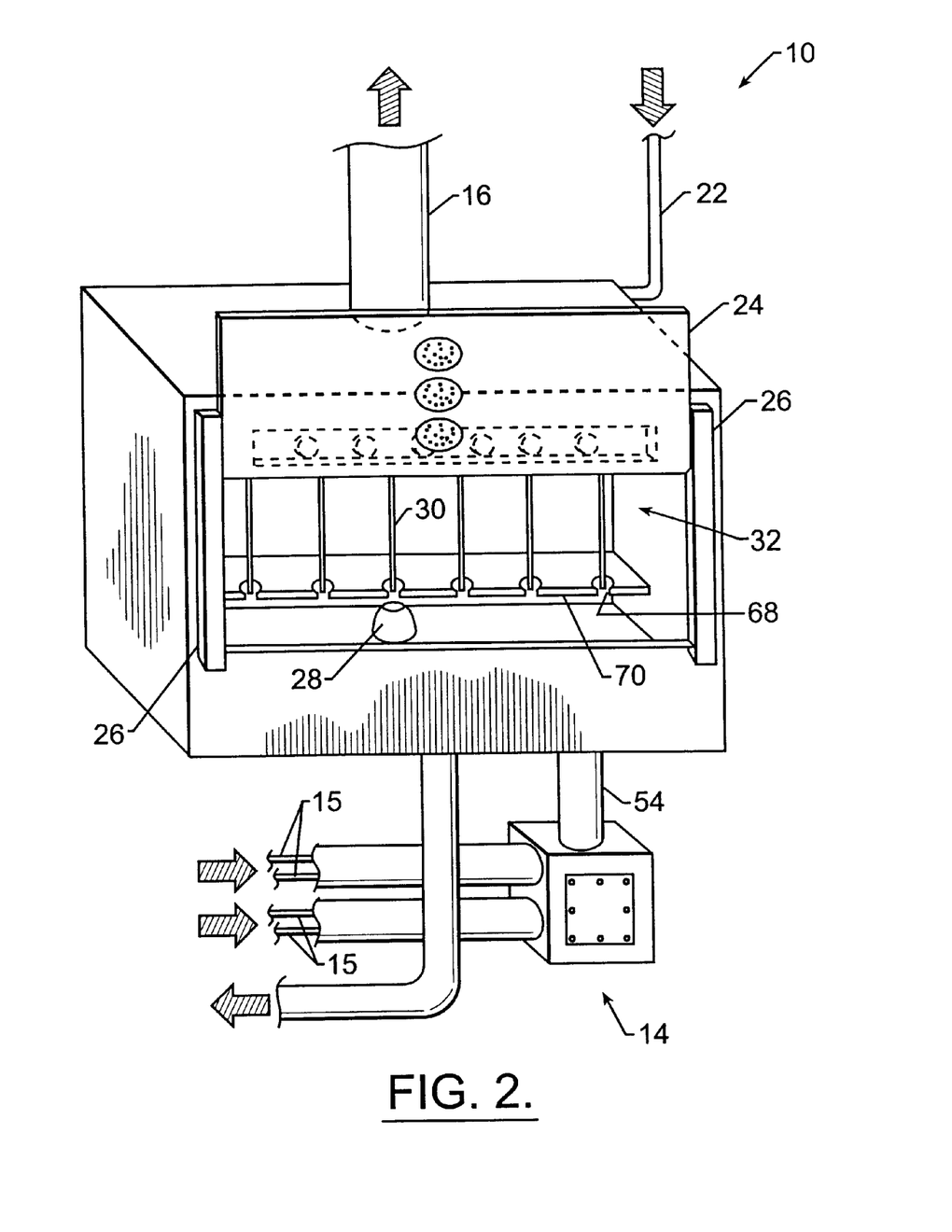
FIG. 2 is an isometric view of the embodiment of FIG. 1, shown with an open door.

As shown in FIG. 2, chemical sampling sink 10 also typically includes an access door 24 configured to vertically slide along tracks 26 between an open configuration shown in FIG. 2, and a closed configuration, shown in FIG. 1. In the closed configuration, access door 24 typically rests in longitudinal slot 26a, shown in FIG. 5. In the open position, access door 24 typically rests in slot 26b, also shown in FIG. 5, and extends upward above the top of the enclosure. Alternatively, the access door may transition in a manner other than vertical sliding, such as by hinges, rotation, horizontal sliding, or other transition mechanism.

When access door 24 is in the open configuration, receptacle 28 may be placed by an operator inside enclosure 12, and positioned adjacent to one of dispensers 30. Dispensers 30 are fed by respective chemical supply lines 15, and are configured to dispense liquid chemical into receptacle 28. After placing the receptacle in the enclosure, the operator may close access door 24 to prevent accidental spillage of the chemical and unwanted entrance of airborne contaminants during the sampling process. Once the access door is closed, liquid chemical may be dispensed through dispenser 30 into receptacle 28 within the substantially contaminant-free interior of enclosure 12. The access door then may be opened, and the sample removed and processed.

Figure 4:
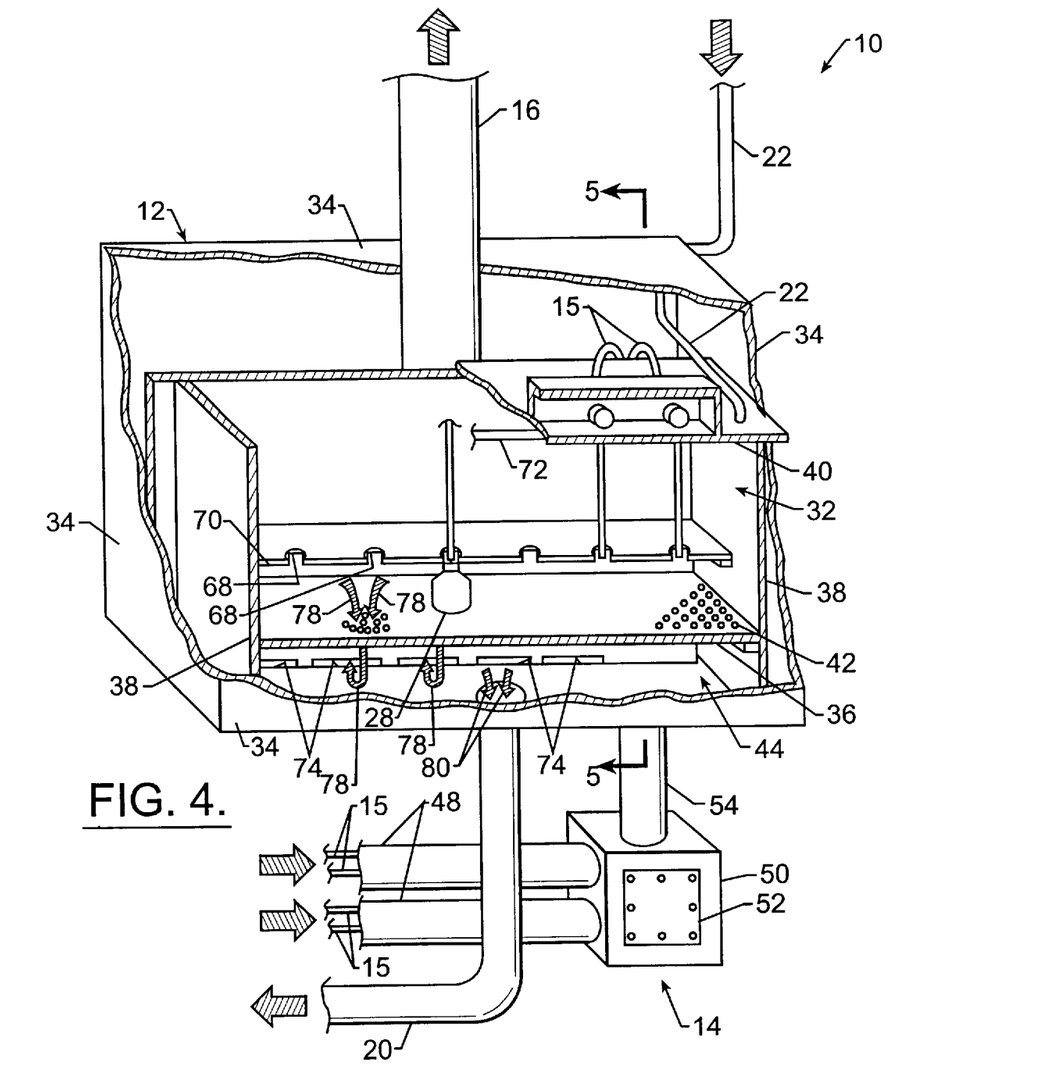
FIG. 4 is a cutaway isometric view of the embodiment of FIG. 1.

As shown in FIG. 4, enclosure 12 also typically includes a sampling compartment 32 positioned in the interior of the enclosure. Sampling compartment 32 typically includes a floor 36, side walls 38, and a ceiling 40. Floor 36 typically is perforated with holes 42 across substantially all of its surface. Alternatively, floor 36 may be perforated only in certain regions, or may contain only one hole or a small number of holes. In addition, floor 36 typically includes large holes 42a, shown in FIG. 8, and may also include holes of various other sizes. The holes in floor 36 are configured to allow liquid chemicals, water, and gases to pass through floor 36 into a lower region 44.

Chemical delivery subsystem 14 typically includes a plurality of chemical supply lines 15 configured to carry a variety of liquid chemicals used in silicon processing, including but not limited to hydrogen peroxide, ammonium hydroxide, acetic acid, nitric acid, hydrofluoric acid, hydrochloric acid, sulfuric acid, potassium hydroxide, sodium hydroxide, and deionized water. Of course, only compatible chemicals should be grouped in a single sampling box. The liquid chemicals are carried from a source (not shown) by chemical supply lines 15, through a plurality of conduits 48 to a service access chamber 50. Service access chamber 50 includes a service door 52 which may be removed to allow an operator easy access to chemical supply lines 15. Chemical supply lines 15 continue from service access chamber 50 upward through a second conduit 54 into a rear right corner of enclosure 12. Alternatively, chemical supply lines 15 may enter into enclosure 12 in another location or manner, such as without conduits 48 and 54 or service access chamber 50.

Typically, chemical supply lines 15 are made from a perfluoroalkoxy (PFA), which is resistant to chemical reaction. Alternatively, another fluoroplastic, or virtually any other material suitable to transport the chemical liquid without contamination or adverse chemical reaction, may be used for chemical supply lines 15.

Figure 6:
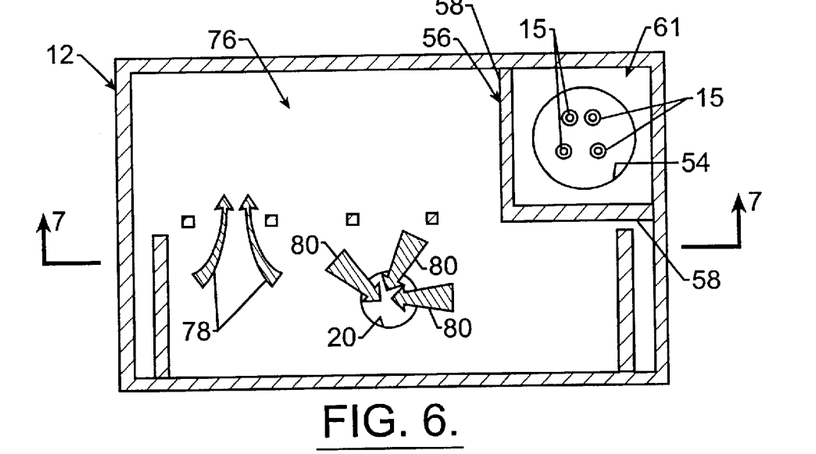
FIG. 6 is a cross-sectional plan view taken along line 6—6 of FIG. 5.
Figure 7:
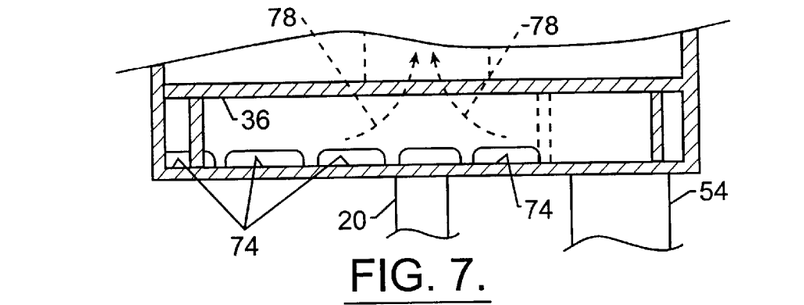
FIG. 7 is a partial cross-sectional elevation view taken along line 7—7 of FIG. 6.
Figure 8:
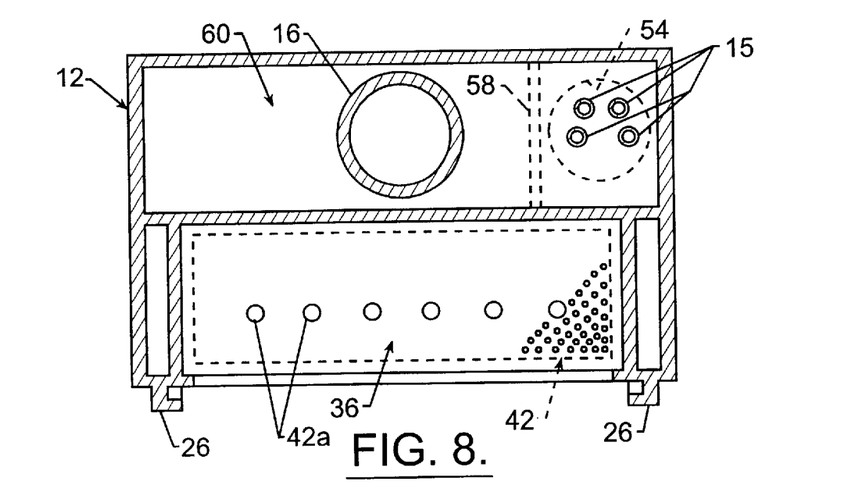
FIG. 8 is a cross-sectional plan view taken along line 8—8 of FIG. 5.

As shown in FIGS. 6–8, chemical supply lines 15 enter enclosure 12 from second conduit 54 into a passthrough chamber 56. Passthrough chamber 56 inhibits passage of drained liquids and gases from enclosure 12 into second conduit 54, and inhibits air from being drawn from second conduit 54 into enclosure 12 by suction from exhaust line 16. Passthrough chamber 56 typically includes walls 58, a ceiling formed by plate 60, shown in FIG. 8, and a floor 61. Chemical supply lines 15 pass through corresponding holes in ceiling 60. Typically, passthrough chamber 56 is separated from the remainder of the enclosure by a substantially airtight seal. Alternatively, a passthrough chamber with no seal may be used, or no passthrough chamber may be employed.

Figure 5:
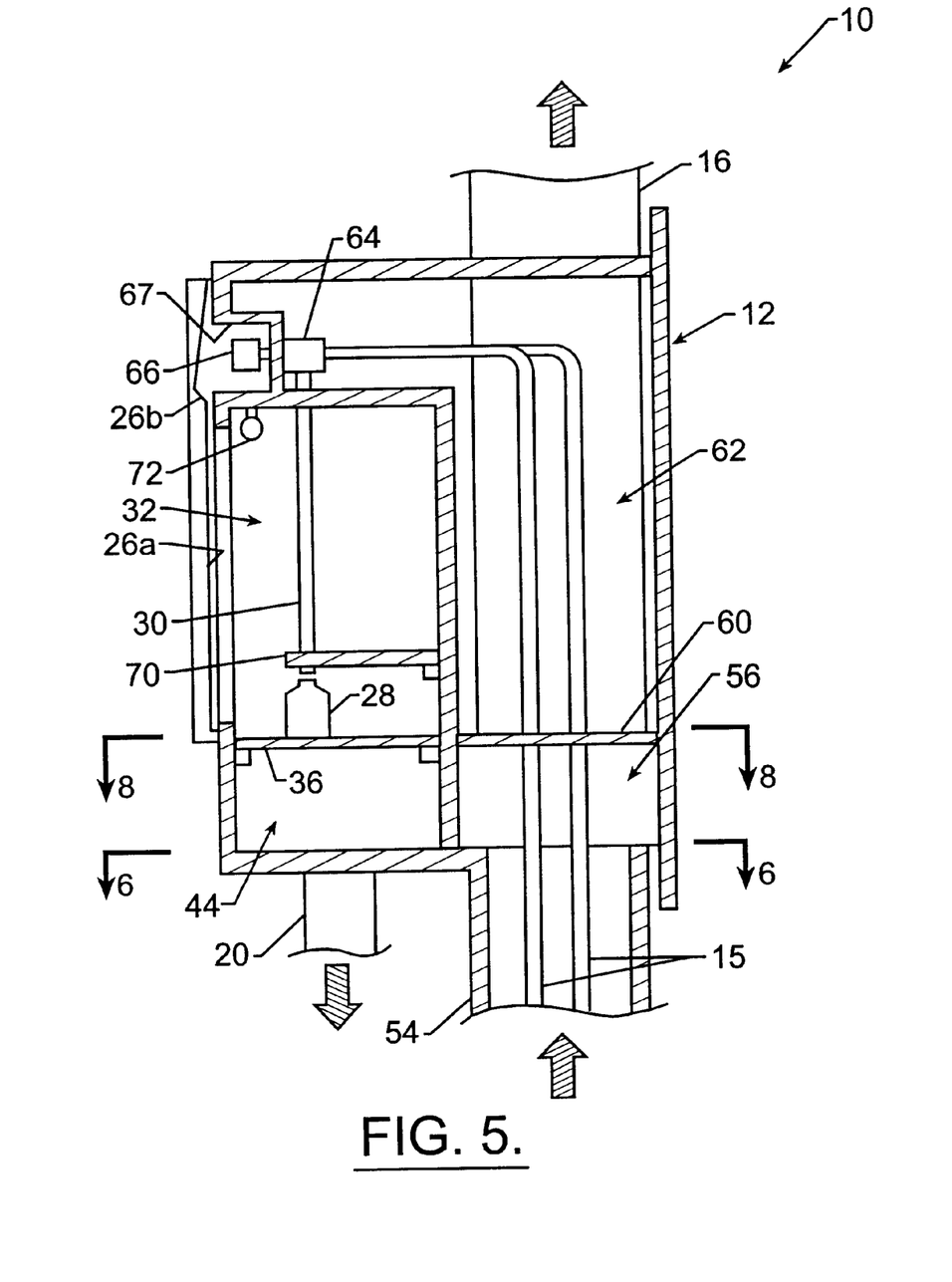
FIG. 5 is a cross-sectional elevation view taken along line 5—5 of FIG. 4.

Turning now to FIG. 5, chemical supply lines 15 continue through passthrough chamber 56 and plate 60 into a rearward chamber 62. Each of chemical supply lines 15 includes a dispenser 30 at an end, and is associated with a corresponding valve 64.

Valves 64 each include an actuator 66 for regulating flow from a chemical supply line 15 to a corresponding dispenser 30. The actuator may be a handle that operates by turning. In one embodiment, valve 64 is a manual PFA two-way valve, sold under the part name MV10-1044-00-01, available from Parker Hannifin Corporation of Cleveland, Ohio. A rotatable handle enables an operator to dispense chemical without continuously depressing a push-button valve, as required by prior sinks. Alternatively, actuator 66 may be a button which operates by pushing in and out, or some other alternative form of actuator, such as a lever. The lever and button also may be configured such that an operator need not hold the lever or button down continuously to dispense chemicals.

Actuators 66 typically are positioned within a recess 67 in the outer surface of enclosure 12. When access door 24 is in the open configuration, the access door covers the recess, and the actuators positioned therein, thereby inhibiting user access to the actuators. Therefore, the access door acts as a safety mechanism, and prevents dispensing of liquid chemical while the access door is open. Alternatively, the actuators may be positioned directly on the outside of the enclosure 12, not in any recess, or in some other location.

Typically, dispenser 30 is a section of PFA tubing attached at a top end to valve 64 and extending into and hanging freely within sampling compartment 32. A lower end of dispenser 30 extends through a notch 68 in a guide plate 70, shown in FIGS. 2 and 4. Guide plate 70 typically is mounted to rear and side walls of sampling chamber 32. In one embodiment of the invention, guide plate 70 is vertically adjustable within sampling compartment 32. Alternatively, the guide plate is fixed at a predetermined height.

The ends of dispensers 30 are configured to be positioned adjacent receptacles 28 when receptacles 28 are placed within the enclosure for sampling. Typically, the dispensers extend to slightly above receptacles 28. Alternatively, the dispensers extend into the receptacles, or are positioned a predetermined distance above the receptacles such that chemical flows from the a dispenser into a receptacle when an actuator 66 of a valve 64 is manipulated.

Chemical sampling sink 10 also may include a sprayer 72, which receives water from water supply line 22, as shown in FIGS. 1 and 4. Typically, sprayer 72 is an elongated spray bar punctuated with holes, such that water sprays out from the bar in various directions into the sampling chamber. The sprayer may be actuated by an external valve (not shown), an actuator in recess 67, or some other control mechanism. For example, water supply line 22 may be routed through one of valves 64 such that the valve may be used to operate the spray bar. In operation, spray bar 72 is configured to spray water throughout sampling chamber 32 to clean any spilled chemicals or other contaminants from the chamber.

Water from the spray bar and liquid chemicals from the dispenser, as well as gases from chemical sampling chamber 32 may pass through perforations or holes 42 in floor 36 and into lower chamber 44. Lower chamber 44 is configured to drain any liquids in the lower chamber down drain line 20. The general flow of liquid down drain 20 is indicated by flow lines 80, in FIG. 4.

Exhaust line 16 is configured to include a suction creating device such a pump or fan (not shown). Exhaust line 16 extends into enclosure 12 through a top of the enclosure and extends through rearward chamber 62 to terminate in plate 60. Plate 60 serves as a ceiling not only for passthrough chamber 56, but also as a ceiling for a manifold chamber 76, shown in FIG. 6. Manifold chamber 76 is separated from passthrough chamber 56 by wall 58. Manifold chamber 76 and multiple passageways 74 direct gases from the lower chamber to the exhaust line.

As gases are drawn out of enclosure 12 by exhaust line 16 and its associated suction source, gases are drawn from chemical sampling chamber 32 down thru-holes or perforations 42 in floor 36 into lower chamber 44, through passageways 74 and into manifold chamber 76 and, finally, up through exhaust line 16 and out of enclosure 12, as shown in FIG. 4. The paths of the gases as they typically flow from the sampling chamber 32 to exhaust line 16 are indicated generally by exhaust flow lines 78.

As air is drawn out of enclosure 12 by exhaust line 16, subatmospheric pressure is created within enclosure 12. The difference in pressure within the enclosure and without the enclosure will tend to draw air into the enclosure from outside the enclosure. Air may enter the enclosure through small gaps, cracks, or imperfect seals in the outer surface, door, joints, etc., of the enclosure.

Figure 9:
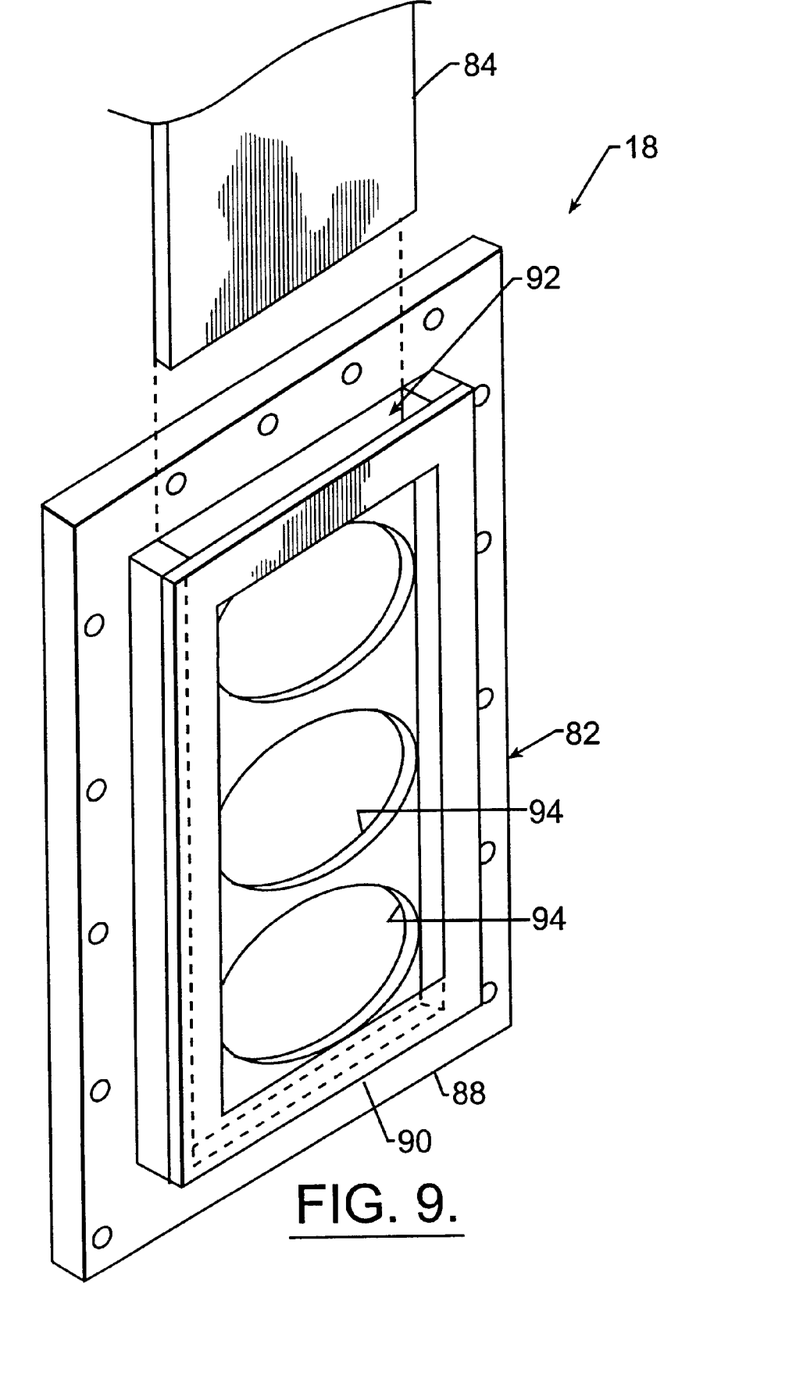
FIG. 9 is an isometric view of one embodiment of a filter assembly according to the present invention.

To prevent airborne contaminants, such as silicon, dust, pollen, etc., from being drawn into the chemical sampling chamber 32 and contaminating a chemical sample, chemical sampling sink 10 includes a filter assembly shown generally at 18 in FIG. 1. As shown in FIG. 9, filter assembly 18 typically includes a filter box 82 configured to house a filter 84. Typically, filter box 82 is positioned inside on the access door of the enclosure, in a position indicated by dashed lines 86 in FIG. 1. Alternatively, filter box 82 may be mounted on an outside of the access door, or elsewhere inside or outside enclosure 12. The filter box may be mounted to the sink in any manner, such as by an adhesive or by screws.

Filter box 82 typically includes a back plate 88 and a framework 90 defining a sheath surrounding void 92. Void 92 is sized to receive filter 84, and is open on one side such that filter 84 may slide out of the framework to be removed and replaced. Back plate 88 typically includes thru-holes 94 which face outward from the enclosure. Alternatively, filter box 82 may be mounted to enclosure such that the thru-holes 94 face into the enclosure 12. Filter 84 alternatively may be mounted to the enclosure without a filter box, for example, by directly mounting the filter in an opening in the enclosure.

Typically, the filter is a standard dust filter. Alternatively, the filter may be a High Efficiency Particulate Air (HEPA) filter. HEPA filters are typically composed of thin pleated sheets of boron silicate microfibers, separated by aluminum separators that direct air flow through the sheets. HEPA filters typically remove about 99.95% of particles 0.3 micrometers or larger in diameter from a quantity of air. In addition, the filter may be another type of filter suitable to remove a larger or smaller percentage of particles of the same or a different size.

Filter assembly 18 is configured to impede airflow into the enclosure substantially less than the combined impedance of other gaps, joints, seals, etc., in the enclosure. Therefore, substantially all of the air drawn into the enclosure usually will pass through filter assembly 18. While typically the filter assembly includes three thru-holes, alternatively the filter assembly may include a larger or smaller number of thru-holes. The thru-holes are depicted as oval in shape, but it should be understood that the thru-holes may be of virtually any size and shape so long as air may pass through the thru-holes through the filter.

Figure 3:
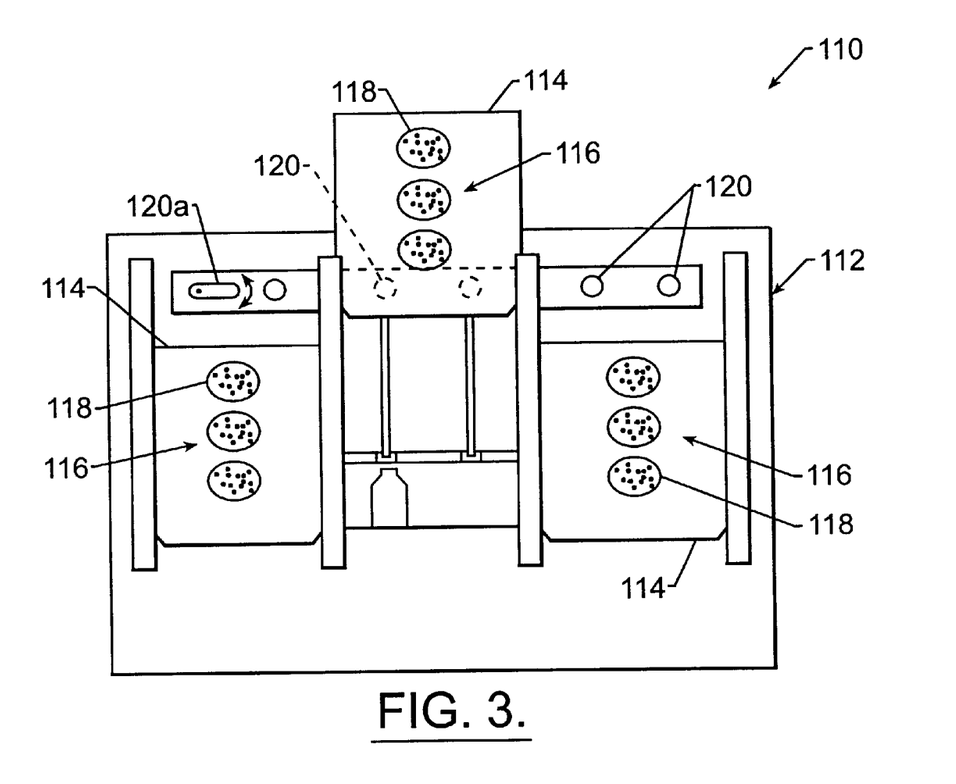
FIG. 3 is a front view of another embodiment of a chemical sampling sink according the present invention.

Referring now to FIG. 3, another embodiment of chemical sampling sink according to the present invention is shown generally at 110. Chemical sampling sink 110 includes an enclosure 112 having a plurality of individually openable access doors 114. Typically, each access door includes a filter assembly 116, each filter assembly having a plurality of thru-holes 118 and an associated filter, as described above. Alternatively, one or more of the doors may not include a filter assembly, and/or the doors may include a filter assembly with a greater or lesser number of thru-holes. When each door 114 is in the open configuration, it is positioned in front of a corresponding set of actuators 120 such that the actuators are difficult or impossible to manipulate when the access door is opened. As shown at 120a, one or more of the actuators may be a lever configured to rotate around a pivot point. Closing the access door exposes the actuators 120, thereby enabling an operator to dispense chemical into a receptacle.

Figure 10:
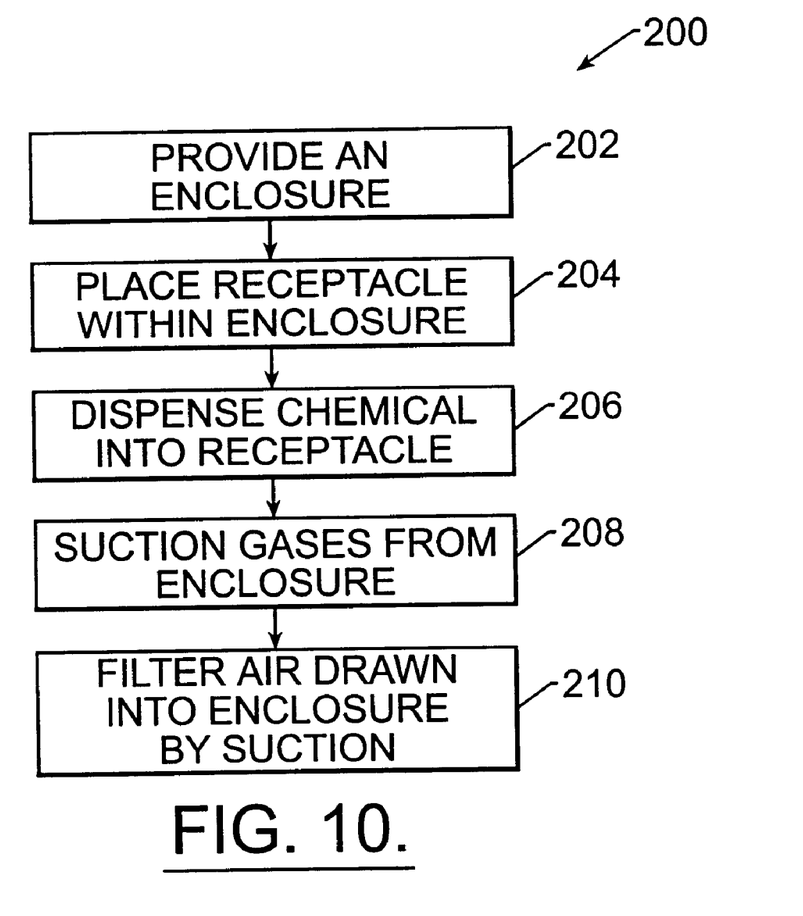
FIG. 10 is a flowchart of a method according to the present invention.

As shown in FIG. 10, a method 200 for sampling a chemical may be practiced according to the present invention. At 202, the method includes providing an enclosure. The enclosure may include an access door, and a filter may be positioned within the access door, or elsewhere on the enclosure, as described above. The enclosure may also include a sampling compartment separated from a lower chamber by a perforated floor, and a manifold chamber fluidically connecting the lower chamber to an exhaust line, as described above.

At 204, the method includes placing a receptacle configured to hold a liquid chemical within the enclosure. Placing may be accomplished by positioning the access door in an open configuration in which the access door at least partially inhibits user access to an actuator of the valve, and inserting the receptacle into the interior of the enclosure adjacent a dispenser. The actuator may be positioned in a recess, and may be a handle or button, as described above.

At 206, the method includes dispensing a chemical through a dispenser into the receptacle within the enclosure. At 208, the method includes suctioning gases from the enclosure to an exhaust line. Suctioning may include drawing air from the sampling compartment to the lower chamber through the perforated floor, from the lower chamber through the manifold chamber, and out the exhaust line. Suctioning may be performed before, after, and/or during the dispensing.

At 210, the method includes filtering air drawn into the enclosure during suctioning. Typically, filtering includes drawing air into the enclosure by suctioning from the exhaust line, and passing air through a filter positioned in a wall of the enclosure. The filtered air typically travels according to the path described above and shown at 208.

According to the present invention, a chemical sampling sink and method are provided that inhibit entry of airborne contaminants air into the enclosure, inhibit dispensation of liquid chemical with an open door, inhibit UV damage to the surface and internal components, and/or may be operated without continuously depressing a button.

Industrial Applicability

This invention is applicable to industrial chemical applications, and particularly to chemical sampling in the semiconductor processing industry.

While the invention has been disclosed in its preferred form or forms, the specific embodiments thereof as disclosed and illustrated herein are not to be considered in a limiting sense as numerous variations are possible. The subject matter of the invention includes all novel and non-obvious combinations and subcombinations of the various elements, features, functions and/or properties disclosed herein. No single feature, function, element or property of the disclosed embodiments is essential. The following claims define certain combinations and subcombinations which are regarded as novel and non-obvious. Other combinations and subcombinations of features, functions, elements and/or properties may be claimed through amendment of the present claims or presentation of new claims in this or a related application. Such claims also are regarded as included within the subject matter of the present invention irrespective of whether they are broader, narrower, equal, or different in scope to the original claims.

We claim:

1. A chemical sampling sink comprising:
    an enclosure defining an internal cavity and configured to maintain an atmosphere within the internal cavity, the enclosure also configured to contain a receptacle such that a liquid chemical within the receptacle would be exposed to the atmosphere, wherein the enclosure is made of dark, UV-resistant plastic;
    a chemical supply line extending into the enclosure, the chemical supply line including a dispenser configured to deliver a liquid chemical to the receptacle;
    an exhaust line attached to the enclosure, the exhaust line being configured to suction gases from the enclosure; and
    a filter positioned on the enclosure, the filter being configured to remove contaminants from air drawn into the enclosure as gases are suctioned from the enclosure out the exhaust line to thereby prevent the removed contaminants from entering the atmosphere in the enclosure and contaminating the liquid chemical in the receptacle.

2. The chemical sampling sink of claim 1, where the enclosure includes a sampling compartment including a perforated floor.

3. The chemical sampling sink of claim 2, further comprising a drain below the perforated floor.

4. The chemical sampling sink of claim 2, where the enclosure includes a lower chamber below the perforated floor, the exhaust line being fluidically connected to the sampling chamber through the perforated floor and lower chamber.

5. The chemical sampling sink of claim 4, where the enclosure further includes a manifold chamber adjacent the lower chamber, the exhaust line being fluidically connected to the sampling compartment through the lower chamber and the manifold chamber.

6. The chemical sampling sink of claim 5, where the manifold chamber is fluidically connected by a plurality of passageways to the lower chamber, and where the exhaust line is configured to suction gases from the enclosure such that air is drawn into the sampling compartment through the filter, from the sampling compartment to the lower chamber through the perforated floor, from the lower chamber to the manifold chamber through the passageways, and out of the enclosure through the exhaust line.

7. The chemical sampling sink of claim 1, where the filter is positioned in a wall of the enclosure.

8. The chemical sampling sink of claim 1, where the enclosure includes an access door and the filter is positioned in the access door.

9. The chemical sampling sink of claim 1, where the enclosure includes a plurality of access doors.

10. The chemical sampling sink of claim 9, further comprising a filter positioned in each access door.

11. The chemical sampling sink of claim 1, where the filter is removably mounted in a filter box.

12. The chemical sampling sink of claim 11, where the filter box includes a plurality of thru-holes through which air may pass.

13. The chemical sampling sink of claim 11, where the filter box includes a sheath configured to hold the filter.

14. The chemical sampling sink of claim 1, where the filter is a HEPA filter.

15. The chemical sampling sink of claim 1, where the enclosure is substantially sealed, such that substantially all of the air drawn into the enclosure as the gases are suctioned out the exhaust line is drawn through the filter.

16. The chemical sampling sink of claim 1, further comprising a valve associated with the chemical supply line, the valve including a rotatable handle configured to regulate flow of liquid chemical through the chemical supply line to the dispenser.

17. The chemical sampling sink of claim 16, where the enclosure includes an access door configured to transition between an open configuration and a closed configuration, the access door being configured to partially cover the rotatable handle when the access door is in the open configuration.

18. A method of sampling a chemical, comprising:
    providing an enclosure defining an internal cavity and configured to maintain an atmosphere within the internal cavity, wherein the enclosure is made of dark, UV-resistant plastic;
    placing a receptacle within the enclosure, the receptacle being configured to hold a chemical such that the chemical within the receptacle is exposed to the atmosphere within the internal cavity;
    dispensing a chemical through a dispenser into the receptacle within the enclosure;
    suctioning gases from the enclosure to an exhaust line; and
    filtering air drawn into the enclosure during suctioning to thereby prevent contaminants from entering the atmosphere within the internal cavity.

19. A chemical sampling sink comprising:
    an enclosure made of dark, UV-resistant plastic;
    a transportable receptacle adapted to be inserted into and removed from the enclosure;
    a chemical supply line extending into the enclosure, the chemical supply line including a dispenser configured to deliver a liquid chemical to the receptacle while the receptacle is disposed in the enclosure;

an exhaust line attached to the enclosure, the exhaust line being configured to suction gases from the enclosure; and filter means for removing contaminants from air drawn into the enclosure as gases are suctioned from the enclosure out the exhaust line.

20. A chemical sampling sink comprising:

an enclosure configured to contain a receptacle;

a chemical supply line extending into the enclosure, the chemical supply line including a dispenser configured to deliver a liquid chemical to the receptacle;

a valve associated with the chemical supply line, the valve including a handle configured to regulate flow of liquid chemical through the chemical supply line to the dispenser;

an access door positioned on the enclosure, the access door being configured to transition between an open configuration and a closed configuration such that the access door at least partially covers the handle when in the open configuration; and an exhaust line attached to the enclosure, the exhaust line being configured to suction gases from the enclosure.

21. The chemical sampling sink of claim 20, where the enclosure is configured to maintain an atmosphere such that a liquid chemical within the receptacle would be exposed to the atmosphere, the chemical sampling sink further comprising a filter positioned on the enclosure and configured to remove contaminants from air drawn into the enclosure as gases are suctioned from the enclosure out the exhaust line to thereby prevent the removed contaminants from entering the atmosphere in the enclosure and contaminating the liquid chemical in the receptacle.

22. A chemical sampling sink comprising:

an enclosure defining an internal cavity and configured to maintain an atmosphere within the internal cavity, the enclosure also configured to contain a receptacle such that a liquid chemical within the receptacle would be exposed to the atmosphere, where the enclosure includes an access door configured to transition between an open configuration and a closed configuration;

a chemical supply line extending into the enclosure, the chemical supply line including a dispenser configured to deliver a liquid chemical to the receptacle;

a valve associated with the chemical supply line, the valve including a rotatable handle configured to regulate flow of liquid chemical through the chemical supply line to the dispenser, where the access door of the enclosure is configured to partially cover the rotatable handle when the access door is in the open configuration;

an exhaust line attached to the enclosure, the exhaust line being configured to suction gases from the enclosure; and a filter positioned on the enclosure, the filter being configured to remove contaminants from air drawn into the enclosure as gases are suctioned from the enclosure out the exhaust line to thereby prevent the removed contaminants from entering the atmosphere in the enclosure and contaminating the liquid chemical in the receptacle.

23. The chemical sampling sink of claim 22, where the enclosure includes a sampling compartment including a perforated floor.

24. The chemical sampling sink of claim 23, further comprising a drain below the perforated floor.

25. The chemical sampling sink of claim 23, where the enclosure includes a lower chamber below the perforated floor, the exhaust line being fluidically connected to the sampling chamber through the perforated floor and lower chamber.

26. The chemical sampling sink of claim 25, where the enclosure further includes a manifold chamber adjacent the lower chamber, the exhaust line being fluidically connected to the sampling compartment through the lower chamber and the manifold chamber.

27. The chemical sampling sink of claim 26, where the manifold chamber is fluidically connected by a plurality of passageways to the lower chamber, and where the exhaust line is configured to suction gases from the enclosure such that air is drawn into the sampling compartment through the filter, from the sampling compartment to the lower chamber through the perforated floor, from the lower chamber to the manifold chamber through the passageways, and out of the enclosure through the exhaust line.

28. The chemical sampling sink of claim 22, where the filter is positioned in a wall of the enclosure.

29. The chemical sampling sink of claim 22, where the enclosure includes an access door and the filter is positioned in the access door.

30. The chemical sampling sink of claim 22, where the enclosure includes a plurality of access doors.

31. The chemical sampling sink of claim 30, further comprising a filter positioned in each access door.

32. The chemical sampling sink of claim 22, where the filter is removably mounted in a filter box.

33. The chemical sampling sink of claim 32, where the filter box includes a plurality of thru-holes through which air may pass.

34. The chemical sampling sink of claim 32, where the filter box includes a sheath configured to hold the filter.

35. The chemical sampling sink of claim 22, where the filter is a HEPA filter.

36. The chemical sampling sink of claim 22, where the enclosure is substantially sealed, such that substantially all of the air drawn into the enclosure as the gases are suctioned out the exhaust line is drawn through the filter.

37. The chemical sampling sink of claim 22, where the enclosure is made of dark, UV-resistant plastic.

38. A chemical sampling sink comprising:

an enclosure, where the enclosure includes an access door configured to transition between an open configuration and a closed configuration;

a transportable receptacle adapted to be inserted into and removed from the enclosure;

a chemical supply line extending into the enclosure, the chemical supply line including a dispenser configured to deliver a liquid chemical to the receptacle while the receptacle is disposed in the enclosure;

a valve associated with the chemical supply line, the valve including a rotatable handle configured to regulate flow of liquid chemical through the chemical supply line to the dispenser, where the access door of the enclosure is configured to partially cover the rotatable handle when the access door is in the open configuration;

an exhaust line attached to the enclosure, the exhaust line being configured to suction gases from the enclosure; and filter means for removing contaminants from air drawn into the enclosure as gases are suctioned from the enclosure out the exhaust line.

* * * * *